US00PP22287P2

(12) United States Plant Patent
Ui et al.

(10) Patent No.: US PP22,287 P2
(45) Date of Patent: Nov. 29, 2011

(54) ***OSTEOSPERMUM* PLANT NAMED 'SAKOST022'**

(50) Latin Name: *Osteospermum hybrida*
Varietal Denomination: SAKOST022

(75) Inventors: Akinobu Ui, Iwata (JP); Shin Ishikawa, Shizuoka (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 12/807,638

(22) Filed: Sep. 10, 2010

(51) Int. Cl.
*A01H 5/00* (2006.01)

(52) U.S. Cl. ..... Plt./360

(58) Field of Classification Search ..... Plt./360
See application file for complete search history.

*Primary Examiner* — Kent L Bell
(74) *Attorney, Agent, or Firm* — Jondle & Associates, P.C.

(57) ABSTRACT

A new *Osteospermum* plant particularly distinguished by having a creamy purple inflorescence color, vigorous growth habit, and an earliness to flower, is disclosed.

1 Drawing Sheet

Genus and species: *Osteospermum hybrida.*
Variety denomination: 'SAKOST022'.

BACKGROUND OF THE NEW PLANT

The present invention comprises a new and distinct cultivar of *Osteospermum*, botanically known as *Osteospermum hybrida*, and hereinafter referred to by the cultivar name 'SAKOST022'. 'SAKOST022' originated as a naturally occuring whole plant mutation from parent 'Pa4Or-33'. 'Pa4Or-33' resulted from a hybridization of proprietary hybrid *Osteospermum* female breeding line 'Pa4' and proprietary hybrid *Osteospermum* male line 'SO-1' in Kakegawa, Japan.

In 2002, the two *Osteospermum* lines were crossed and 127 ovules were removed from flowers on the female parent and cultured by standard ovule culture techniques. A total of thirty-three plantlets were developed. The thirty-three $F_1$ hybrid plantlets were transplanted to soilless media for greenhouse culture and acclimatization. The plants were evaluated in pots. Out of the thirty-three $F_1$ lines, line 'Pa4Or-33' was selected which had vigorous performance and had an early flowering habit.

In 2004, line 'Pa4Or-33' was vegetatively propagated via cuttings and evaluated for performance in a greenhouse. A plant was selected which had a creamy purple flower color and a more compact habit than 'Pa4Or-33'. In the same year, the new plant selection was propagated via vegetative cuttings in an open field and in a greenhouse in Kakegawa, Japan and it was confirmed the plant's characteristics were fixed.

In 2005, the new plant selection was propagated again via vegetative cuttings in an open field and in a greenhouse and confirmed the stability of the distinct characteristics of this variety. The selection subsequently was named 'SAKOST022' and found to reproduce true to type in successive generations of asexual propagation.

SUMMARY OF THE INVENTION

The following are the most outstanding and distinguishing characteristics of this new cultivar when grown under normal horticultural practices in Salinas, Calif.

1. creamy purple flower color;
2. vigorous growth habit; and
3. earliness to flower.

DESCRIPTION OF PHOTOGRAPHS

This new *Osteospermum* plant is illustrated by the accompanying photographs which show the plant's overall plant habit including form, foliage, and flowers. The photographs are of a plant grown three months from transplant date into 6-inch pots from rooted cuttings in Salinas, Calif. in the spring of 2010. The colors shown are as true as can be reasonably obtained by conventional photographic procedures.

DESCRIPTION OF THE NEW CULTIVAR

Figure 1:
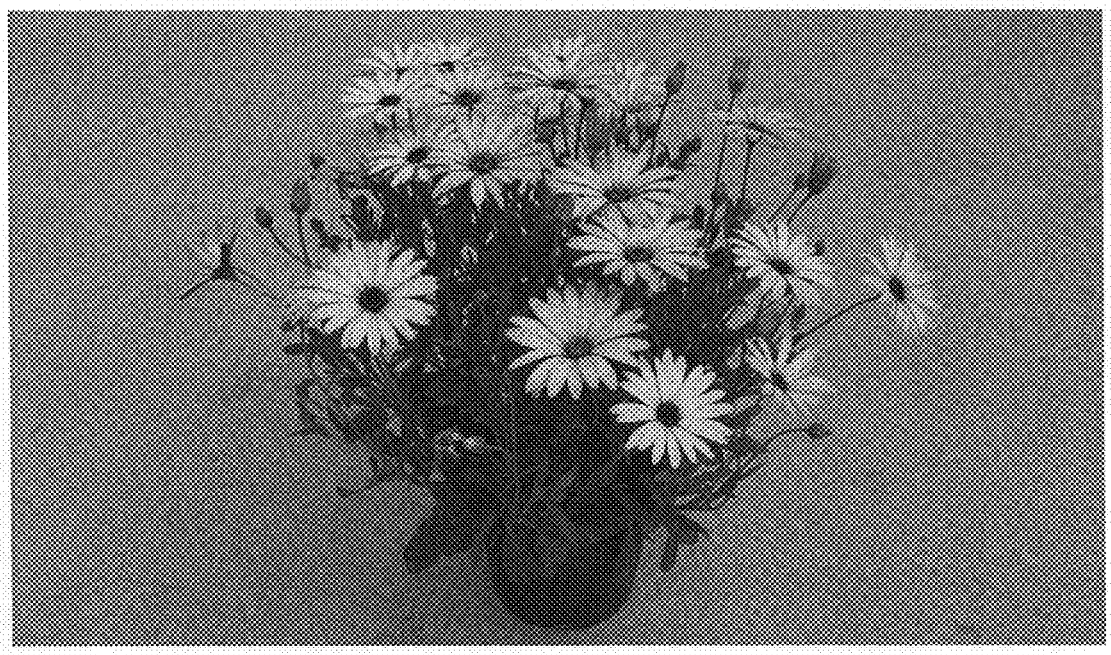
FIG. 1 shows overall plant habit of the plant grown in a pot.
Figure 2:
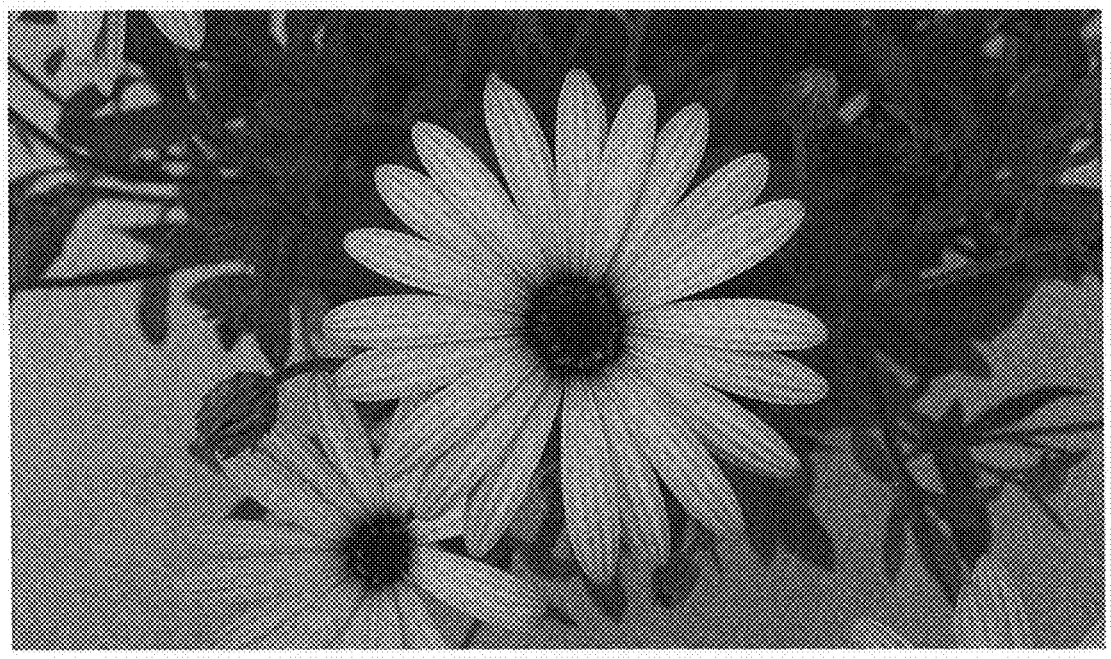
FIG. 2 shows the mature inflorescence of the plant.

The following detailed descriptions set forth the distinctive characteristics of 'SAKOST022'. The data which define these characteristics were collected from asexual reproductions carried out in Salinas, Calif. Data was collected on plants grown approximately three months from transplant date into 6-inch pots under greenhouse conditions in Salinas, Calif. in the spring of 2010. Color references are to The R.H.S. Colour Chart of The Royal Horticultural Society of London (R.H.S.), $4^{th}$ edition.

DESCRIPTION OF THE NEW PLANT

Classification:
- *Family.*—Compositae.
- *Botanical.*—*Osteospermum hybrida.*
- *Common.*—*Osteospermum*, Cape Daisy, South African Daisy.
- *Designation.*—'SAKOST022'.

Parentage:
- *Parent.*—*Osteospermum* plant 'Pa4Or-33' (unpatented).

Growth:
- *Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of Dip 'N Grow root inducing solution in water. The trays are misted hourly during rooting.

*Environmental conditions for plant growth.*—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height they are pinched back to 5 to 6 leaves to promote branching. Spring and summer daytime high temperatures in Salinas, Calif., where the data was collected, range from 16° C. to 25° C.

*Time to bloom from propagation.*—Approximately four weeks when rooted vegetative cuttings are transferred to a 16 cm diameter pot. Flowering season is all year in the United States. Vernalization is not required to induce flowering.

Plant description:

*Habit.*—Vigorous.
*Life cycle.*—Perennial.
*Form.*—Erect.
*Height (from soil line to top of foliage).*—33.0 cm to 34.0 cm.
*Width.*—48.0 cm to 50.0 cm.

Stems:

*General.*—Circular in cross section; dull.
*Stem length (total).*—9.0 cm to 10.0 cm.
*Diameter.*—0.3 cm.
*Internode length.*—1.0 cm.
*Color.*—RHS 144A (Yellow-green).
*Pubescence.*—Slight. Color: RHS N155A (White). Shape: Linear.
*Anthocyanin color.*—None.

Branches:

*General.*—Smooth, circular cross-section.
*Number of main branches.*—One.
*Total number of branches.*—Four.
*Length.*—1.0 cm from soil line to first node.
*Diameter.*—0.5 cm.
*Internode length.*—2.0 cm.
*Color.*—RHS 144A (Yellow-green); anthocyanin is absent.
*Pubescence.*—Absent.

Leaves:

*Arrangement.*—Alternate.
*Shape.*—Oblanceolate.
*Apex.*—Acute.
*Base.*—Attenuate.
*Margin.*—Serrate.
*Venation.*—Pinnate.
*Surface (both surfaces).*—Dull; smooth.
*Surface pubescence (both surfaces).*—Absent.
*Attachment.*—Decurrant.
*Length.*—7.0 cm.
*Width.*—3.0 cm.
*Thickness.*—Less than 0.1 cm.
*Color.*—Upper surface: RHS 137A (Green). Lower surface: RHS 138B (Green).
*Venation color.*—Upper surface: RHS 144A (Yellow-green). Lower surface: RHS 144B (Yellow-green).

Inflorescence:

*Number per plant.*—28 with multiple buds.
*Type.*—Capitulum (head); disc florets are perfect and ray florets are carpellate.
*Flowering habit.*—Determinate.
*Lastingness of inflorescences.*—3 to 4 days.
*Fragrance.*—Absent.
*Seed production.*—None observed.
*Diameter.*—8.0 cm.
*Depth.*—1.0 cm.
*Petal (ray floret) number.*—20 to 22 per inflorescence.
*Disc diameter.*—1.5 cm.
*Disc floret number.*—60 to 80 per inflorescence.
*Peduncle length.*—12.0 cm.
*Peduncle diameter.*—0.2 cm.
*Peduncle color.*—RHS 144A (Yellow-green).
*Peduncle texture.*—Dull; slight pubescence.
*Phyllaries.*—Arrangement: 19 per inflorescence; free; arranged symmetrically. Length: 1.0 cm to 1.2 cm. Width: 0.15 cm. Apex: Acute. Margin: Entire. Shape: Linear; acute. Color: Upper surface: RHS 137A (Green). Lower surface: RHS 137A (Green).

Ray florets (ligules):

*Corolla.*—One ray per ray floret; only the outer row of florets are the ray florets.
*Number of ray florets.*—20 to 22 per inflorescence.
*Length.*—4.0 cm.
*Width.*—0.9 cm.
*Shape.*—Lanceolate.
*Apex.*—Obtuse with a notched tip.
*Margin.*—Entire.
*Base.*—Fused.
*Color.*—Upper surface: RHS 75A (Purple) stripes with RHS N155B (White) blotches and RHS N88A (Violet) at base. Lower surface: RHS 160A (Greyed-yellow) with stripes of RHS N187A and N187B (Greyed-purple).
*Pubescence.*—Glabrous.

Disc florets:

*Color.*—RHS 155A (White) with RHS N88A (Violet) at tip.
*Shape.*—Tubular.
*Apex.*—Rounded.
*Surface.*—Smooth; shiny.
*Size.*—Length: 0.7 cm. Width: 0.1 cm.

Reproductive organs:

*Ovary.*—Superior.
*Pistil form.*—One style with two stigma branches.
*Pistil length.*—0.3 cm.
*Stigma color.*—RHS N187A (Greyed-purple).
*Style color.*—RHS 75A (Purple).
*Stamens.*—5; fused into a single tube.
*Anther color.*—RHS N187A (Greyed-purple).
*Pollen color.*—RHS 23A (Yellow-orange).
*Filament color.*—RHS 155A (White).

Disease and insect resistance: Very disease resistant. However, plants are susceptible to aphids, thrips, whiteflies, and worms.

COMPARISON WITH PARENTAL LINES AND KNOWN CULTIVAR

'SAKOST022' is a distinct variety of *Osteospermum* owing to its creamy purple color, vigorous growth habit, and earliness to flower. 'SAKOST022' is distinguished from its parent and grandparents as described in Table 1 (color references are to The Royal Horticultural Society Colour Chart, 4th edition):

TABLE 1

Comparison with Parental Lines

| Characteristic | 'SAKOST022' | Parent 'Pa4Or-33' | Male Grandparent 'SO-1' | Female Grandparent 'PA4' |
|---|---|---|---|---|
| Ray floret (ligule) color, upper surface | Creamy purple | Mosaic purple pattern on cream color | Pink | Purple |
| Plant growth habit | Vigorous | More vigorous | Compact | Vigorous |

'SAKOST022' is a distinct variety of *Osteospermum* owing to its creamy purple color, vigorous growth habit, and earliness to flower. 'SAKOST022' is most similar to the *Osteospermum* plant named 'Osjamlipur' (U.S. Plant Pat. No. 17,410). Differences between the two varieties are described in Table 2 (color references are to The Royal Horticultural Society Colour Chart, 4th edition):

TABLE 2

Comparison with Similar Variety

| Characteristic | 'SAKOST022' | 'Osjamlipur' |
|---|---|---|
| Ray floret (ligule) color, upper surface | RHS 75A (Purple) stripes with blotches of RHS N155B (White) and RHS N88A (Violet) at base | RHS 77C (Purple) tips with RHS 77D (Purple) at center and RHS N155B (White) at base |
| Plant growth habit | Vigorous and early to flower | Compact and round |

We claim:

1. A new and distinct cultivar of *Osteospermum* plant as shown and described herein.

* * * * *